(12) United States Patent
Zhao

(10) Patent No.: US 12,303,294 B2
(45) Date of Patent: May 20, 2025

(54) MONITOR PAD AND BODY STATUS MONITORING SYSTEM

(71) Applicant: Goertek Inc., Shandong (CN)

(72) Inventor: Bosen Zhao, Shandong (CN)

(73) Assignee: Goertek Inc., Weifang (CN)

( * ) Notice: Subject to any disclaimer, the term of this patent is extended or adjusted under 35 U.S.C. 154(b) by 704 days.

(21) Appl. No.: 17/333,355

(22) Filed: May 28, 2021

(65) Prior Publication Data

US 2022/0378374 A1  Dec. 1, 2022

(51) Int. Cl.
| | | |
|---|---|---|
| *A61B 5/00* | (2006.01) | |
| *A61B 5/0205* | (2006.01) | |
| *A61B 7/00* | (2006.01) | |
| *A61B 7/04* | (2006.01) | |
| *H02J 7/04* | (2006.01) | |
| *H02J 50/10* | (2016.01) | |
| *H04B 5/79* | (2024.01) | |
| *A61B 5/024* | (2006.01) | |
| *A61B 5/08* | (2006.01) | |

(52) U.S. Cl.
CPC .......... *A61B 5/6892* (2013.01); *A61B 5/0205* (2013.01); *A61B 7/003* (2013.01); *A61B 7/04* (2013.01); *H02J 7/04* (2013.01); *H02J 50/10* (2016.02); *H04B 5/79* (2024.01); *A61B 5/024* (2013.01); *A61B 5/0816* (2013.01); *A61B 2560/0214* (2013.01)

(58) Field of Classification Search
CPC ..... A61B 5/6892; A61B 5/0205; A61B 7/003; A61B 7/04; A61B 5/024; A61B 5/0816; A61B 2560/0214; H02J 7/04; H02J 50/10; H04B 5/79
See application file for complete search history.

(56) References Cited

U.S. PATENT DOCUMENTS

| | | | |
|---|---|---|---|
| 9,591,995 B2* | 3/2017 | Blumberg | A47C 17/62 |
| 9,977,865 B1* | 5/2018 | LaBorde | G06K 7/10366 |
| 10,201,935 B2* | 2/2019 | Augustine | B23K 13/00 |
| 2003/0095263 A1* | 5/2003 | Varshneya | A61B 5/6892 |
| | | | 356/477 |
| 2008/0001735 A1* | 1/2008 | Tran | A61B 5/6806 |
| | | | 340/539.22 |
| 2013/0165993 A1* | 6/2013 | Aghassian | A61N 1/36128 |
| | | | 607/59 |
| 2014/0101848 A1* | 4/2014 | Murphy | A47G 9/08 |
| | | | 5/420 |
| 2015/0094914 A1* | 4/2015 | Abreu | B60H 1/00742 |
| | | | 701/1 |
| 2016/0294040 A1* | 10/2016 | Blair | H01Q 7/00 |
| 2018/0177486 A1* | 6/2018 | Gifford, III | A61B 8/12 |
| 2021/0022621 A1* | 1/2021 | Sullivan | A61B 5/6891 |
| 2021/0244377 A1* | 8/2021 | Amoh | A61B 5/7257 |
| 2023/0238827 A1* | 7/2023 | Borelli | H02J 50/001 |
| | | | 307/104 |

\* cited by examiner

*Primary Examiner* — Catherine M Voorhees
(74) *Attorney, Agent, or Firm* — Baker Botts LLP

(57) ABSTRACT

Here disclose a monitor pad and a body status monitoring system. The monitor pad includes: a pad cover, a padding, a microphone and a transmission circuit, wherein, the microphone is placed in the padding and is used to detect body information of a person adjacent to the monitor pad, and the transmission circuit transmits the body information to an external processing device.

10 Claims, 11 Drawing Sheets

MONITOR PAD AND BODY STATUS MONITORING SYSTEM

FIELD OF THE INVENTION

The embodiments disclosed herein relate to the technical field of body monitoring, and in particular, to a monitor pad and a body status monitoring system.

BACKGROUND OF THE INVENTION

Currently, an equipment used to monitor a user's body requires the user to wear additional monitoring devices. These additional monitoring devices are, for example, sensors or watches and so on. These additional monitoring devices often do not increase the user's comfort and may increase the user's burden. For example, a smart watch worn on the wrist and/or a sensor attached to the user's body may make the user feel uncomfortable under certain circumstances.

U.S. Pat. No. 9,943,261 B2 discloses a method and apparatus for improving and monitoring sleep, which is incorporated herein by reference in its entirety.

U.S. Pat. No. 9,839,563 B2 discloses an infant patient transfer device with heart rate sensor, which is fully incorporated herein by reference.

U.S. Pat. No. 9,655,532 B2 discloses a wearable physiological monitoring and notification system based on real-time heart rate variability analysis, which is fully incorporated herein by reference.

The U.S. design Pat. D796,046 S discloses a sensor, which is incorporated herein by reference in its entirety.

U.S. Pat. No. 9,451,905 B2 discloses a method and apparatus for monitoring the baroreceptor reflex of a user, which is incorporated herein by reference in its entirety.

U.S. Pat. No. 9,713,430 B2 discloses acoustic sensors for abdominal cardiac activity detection, which is hereby incorporated by reference in its entirety.

U.S. Pat. No. 9,882,610 B1 discloses a near field communication sensor system, which is incorporated herein by reference in its entirety.

U.S. Pat. No. 9,900,677 B2 discloses a system for continuous monitoring of body sounds, which is hereby incorporated by reference in its entirety.

U.S. Pat. No. 9,943,261 B2 discloses a method and apparatus for improving and monitoring sleep, which is hereby incorporated by reference in its entirety.

SUMMARY OF THE INVENTION

One object of this invention is to provide a new technical solution for body monitoring.

According to a first aspect of this disclosure, there is provided a monitor pad, including: a pad cover, a padding, a microphone and a transmission circuit, wherein, the microphone is placed in the padding and is used to detect body information of a person adjacent to the monitor pad, and the transmission circuit transmits the body information to an external processing device.

According to a second aspect of this disclosure, there is provided a body status monitoring system, including: the monitor pad according to embodiments; an external processing device; and a network server, wherein the monitor pad detects body information of a person and sends the detected body information to an external processing device, and the external processing device forwards the body information to the network server to analyze the body information.

According to the embodiments of this disclosure, physical status of a user can be monitored while providing the user with a comfortable feeling.

Further features of the disclosure and advantages thereof will become apparent from the following detailed description of exemplary embodiments according to the disclosure with reference to the attached drawings.

BRIEF DESCRIPTION OF THE DRAWINGS

The accompanying drawings, which are incorporated in and constitute a part of the specification, illustrate embodiments of the invention and, together with the description thereof, serve to explain the principles of the invention.

DETAILED DESCRIPTION OF THE EMBODIMENTS

Figure 1:
FIG. 1 shows a photo of a monitor pad according to an embodiment of this disclosure.

Various exemplary embodiments of the disclosure will now be described in detail with reference to the drawings. It should be noted that the relative arrangement of the components and steps, the numerical expressions, and numerical values set forth in these embodiments do not limit the scope of the disclosure unless it is specifically stated otherwise.

The following description of at least one exemplary embodiment is merely illustrative in nature and is in no way intended to limit the invention, its application, or uses.

Techniques, methods and apparatus as known by one of ordinary skill in the relevant art may not be discussed in detail but are intended to be part of the specification where appropriate.

In all of the examples illustrated and discussed herein, any specific values should be interpreted to be illustrative only and non-limiting. Thus, other examples of the exemplary embodiments could have different values.

Notice that similar reference numerals and letters refer to similar items in the following figures, and thus once an item is defined in one figure, it is possible that it need not be further discussed for following figures.

Figure 2:
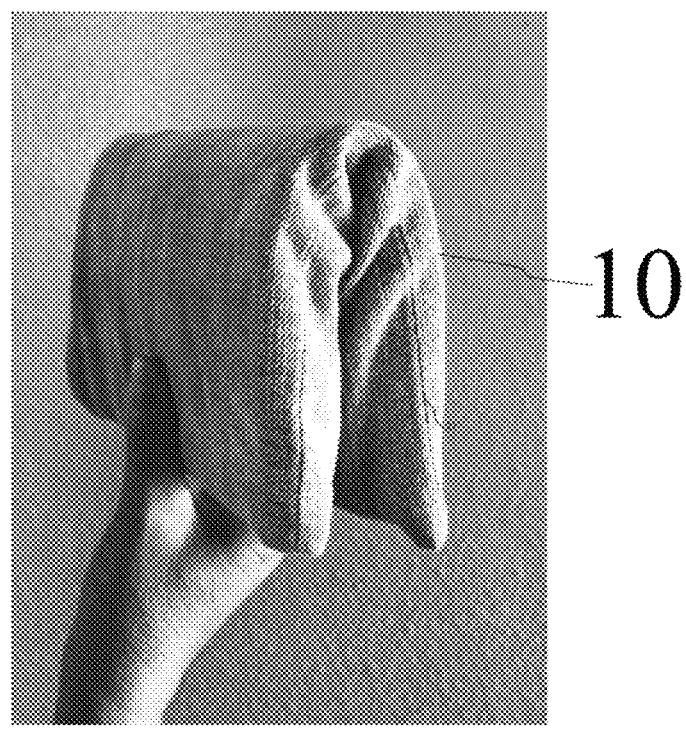
FIG. 2 shows a photo of a monitor pad in a folded state according to an embodiment of this disclosure.

FIG. 1 shows a photo of a monitor pad 10 according to an embodiment of this disclosure. FIG. 2 shows a photo of the monitor pad 10 in a folded state according to an embodiment of this disclosure. As shown in FIGS. 1 and 2, the monitor pad 10 is soft and foldable.

The monitoring pad 10 may include a pad cover, a padding, a microphone, and a transmission circuit. The microphone is placed in the padding and used to detect the body information of a person adjacent to the monitor pad. The transmission circuit sends the body information to an external processing device. The body information may include at least one of a person's heartbeat signal and breathing vibration signal, for example. The external processing device can be smart phones, laptops, tablet computers, dedicated monitoring terminal equipment, etc. The processing device can directly process the received body information and generate monitoring results, for example, the user's breathing rate, heart rate, etc. The processing device can also send body information to a server on the network. The server processes the body information and returns the processing result to the processing device.

Generally, a user's body monitoring device becomes a burden when the user uses it. For example, sensors of some monitoring devices need to be attached to the user's body during usage, or wearable devices such as smart watches need to be worn on the user's body. When the user uses these monitoring devices, these devices will not increase the user's comfort feeling. For the design of these devices, what a designer considers most is how to reduce the user's discomfort when using it. However, in any case, the use of these devices will cause a certain burden to the user to a certain extent, or will not increase the user's comfort. The inventor proposes a new design direction to monitor the user's physical body status while increasing the user's comfort. The monitor pad here can be used as a seat cushion.

As shown in FIG. 2, the monitor pad 10 is foldable, which makes it easier to carry. A user can carry it with him during travels or business trips to relieve fatigue during the journey. Optionally, the length of the monitor pad 10 is less than or equal to 420 mm and the width thereof is less than or equal to 297 mm. In this case, the size of the monitor pad 10 after being folded is similar to that of an A4 paper, which makes it easier for a user to carry it with him. For example, it can be placed in the user's briefcase.

Hereinafter, various embodiments and application scenarios of the monitor pad will be described with reference to FIGS. 3-13.

Figure 3:
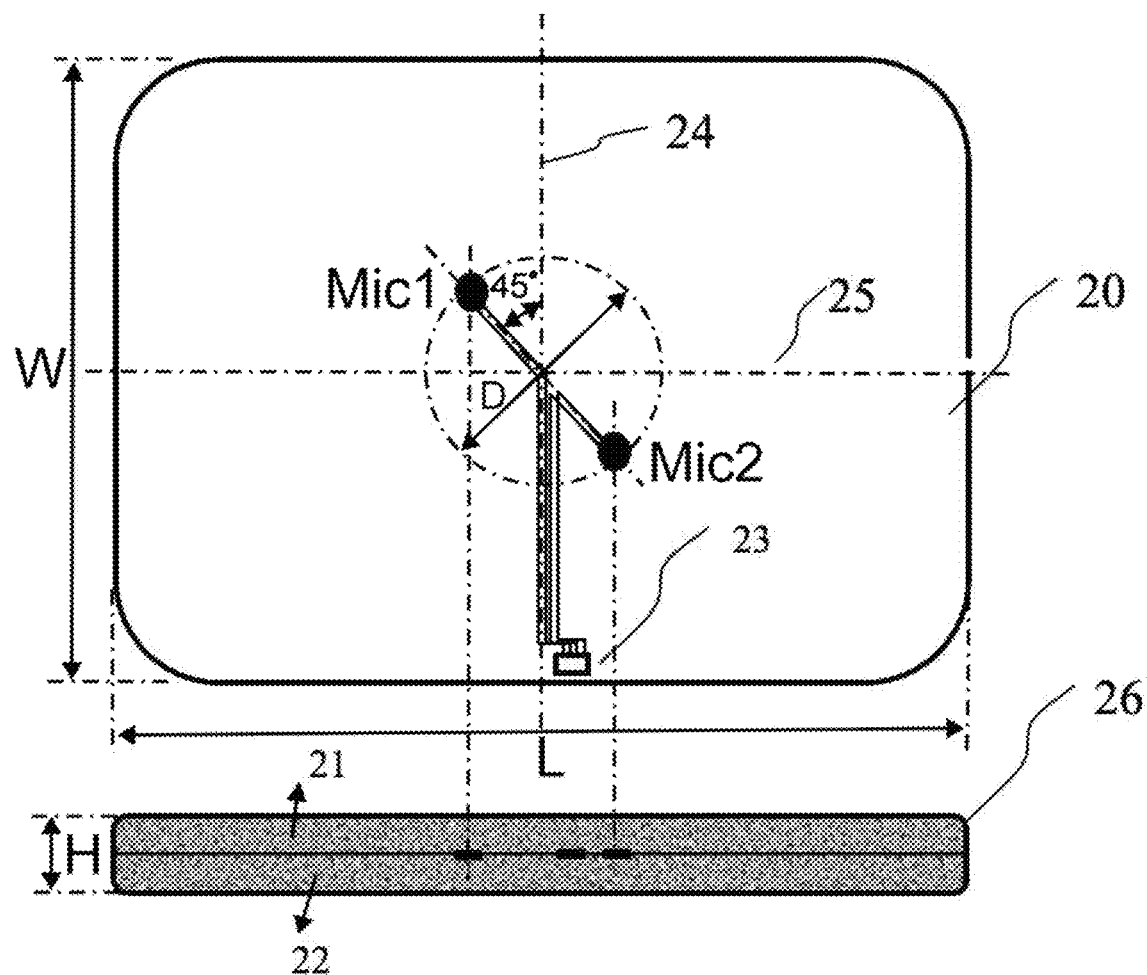
FIG. 3 shows a schematic structural diagram of a monitor pad according to an embodiment of this disclosure.

FIG. 3 shows a schematic structural diagram of a monitor pad according to an embodiment of this disclosure.

Two microphones Mic 1 and Mic 2 are shown in FIG. 3. The microphones Mic 1 and Mic 2 may be micro-electro-mechanical system (MEMS) microphones, for example. In FIG. 3, the microphones Mic 1 and Mic 2 are located outside the short axis 24 and the long axis 25 of the monitor pad 20. For example, in FIG. 3, the microphones Mic 1 and Mic 2 are symmetrical with respect to the center of the monitor pad 20 and have an angle of 45 degrees with the short axis 24 or the long axis 25, respectively. In this case, on the one hand, the two microphones Mic 1 and Mic 2 can establish a larger detection range; on the other hand, when the monitor pad 20 is folded along the short axis 24 or the long axis 25 (which usually happens), the two microphones Mic 1 and Mic 2 are not easily damaged.

In FIG. 3, the transmission circuit includes a connector 23. The microphones Mic 1 and Mic 2 are connected to the connector 23. The connector 23 is used to connect with an external processing device to send body information to the processing device.

As shown in FIG. 3, the length L of the monitor pad 20 may be less than or equal to 420 mm and the width W may be less than or equal to 297 mm.

A side view of the monitor pad 20 is shown at the bottom of FIG. 3. As can be seen from the side view, the monitor pad 20 has a height H. The pad cover 26 of the monitor pad 20 covers the inner padding. In FIG. 3, the padding includes an upper padding 21 and a lower padding 22. Optionally, the microphones Mic 1 and Mic 2 and the connector 23 may be located between the upper padding 21 and the lower padding 22, so that the upper padding 21 and the lower padding 22 can protect the microphones Mic 1 and Mic 2 and the connector 23.

Figure 4:
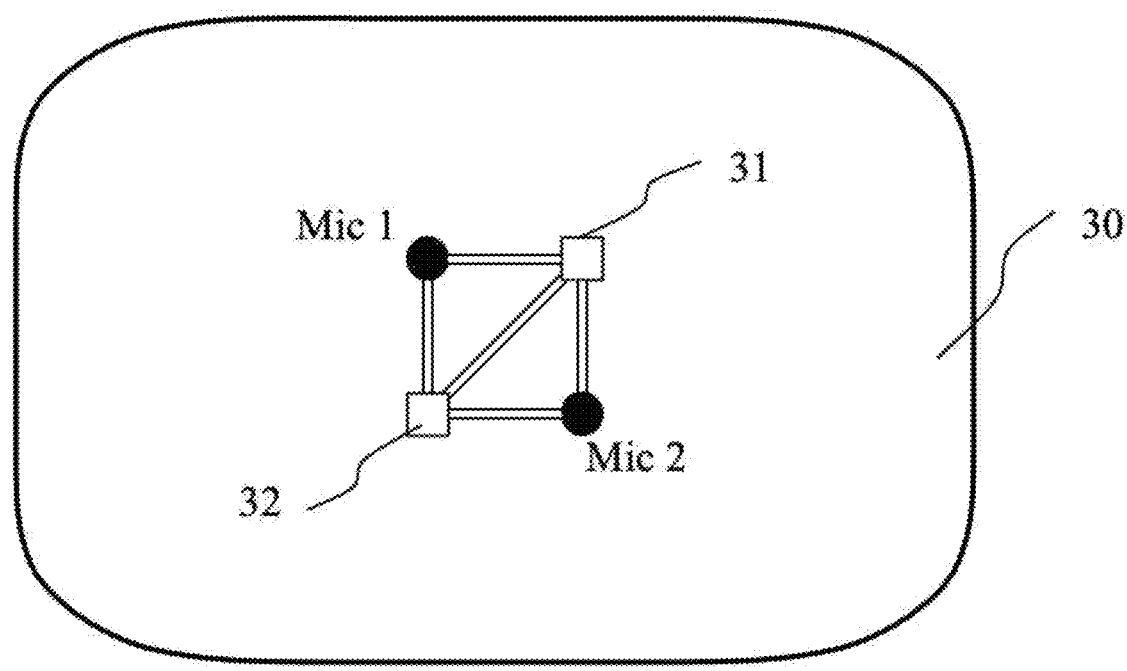
FIG. 4 shows a schematic structural diagram of a monitor pad according to another embodiment of this disclosure.

FIG. 4 shows a schematic structural diagram of a monitor pad according to another embodiment of this disclosure. As shown in FIG. 4, the monitor pad 30 includes microphones Mic 1 and Mic 2 and a battery 32. The transmission circuit includes a wireless transmission device 31.

The microphones Mic 1 and Mic 2 and the wireless transmission device 31 are connected to the battery 32 to receive power. The microphones Mic 1 and Mic 2 are connected to the wireless transmission device 31 and transmit body information to an external processing device via the wireless transmission device 31.

In this embodiment, there is no need to supply power to the devices in the monitor pad in a wired manner. This can improve the mobility of the monitor pad 30, which is convenient for a user to carry and use in different locations.

Figure 5:
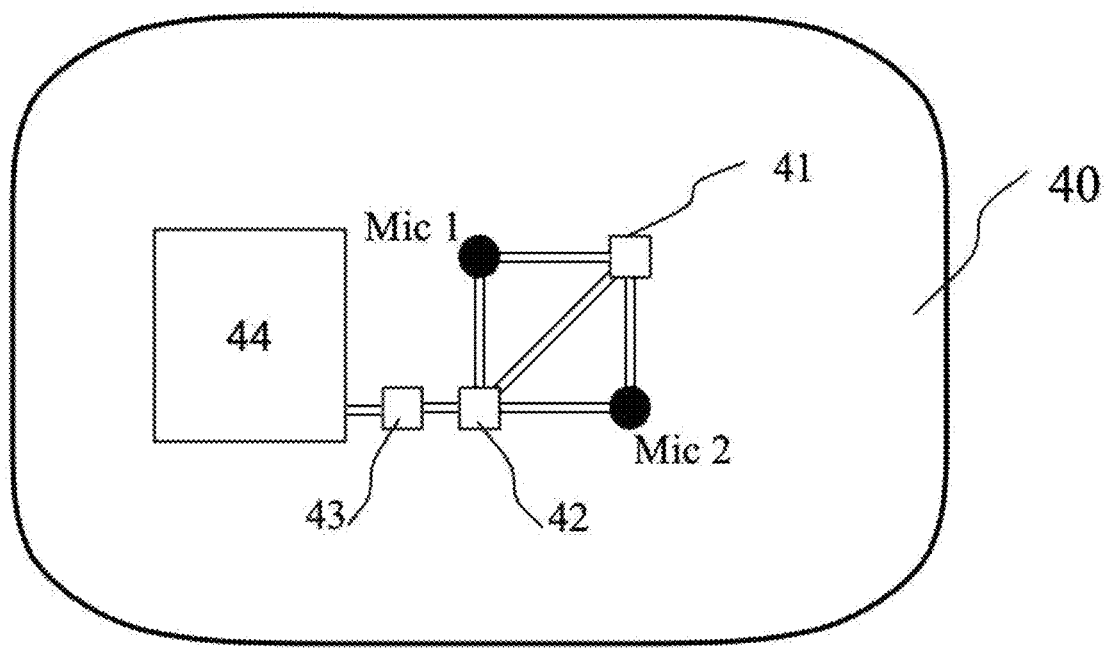
FIG. 5 shows a schematic structural diagram of a monitor pad according to another embodiment of this disclosure.

FIG. 5 shows a schematic structural diagram of a monitor pad according to another embodiment of this disclosure. In the embodiment of FIG. 5, the monitor pad 40 includes microphones Mic 1 and Mic 2 and a rechargeable battery 42. The transmission circuit includes a wireless transmission device 41.

The microphones Mic 1 and Mic 2 and the wireless transmission device 41 are connected to the rechargeable battery 42 to receive power. The microphones Mic 1 and Mic 2 are connected to the wireless transmission device 41 and send body information to an external processing device via the wireless transmission device 41.

In addition, the monitor pad 40 also includes a power receiving coil 44 and a rectifying circuit 43. The power receiving coil 44 receives an external electromagnetic signal, and the rectifier circuit 43 converts the electromagnetic signal into direct current. The direct current is supplied to the rechargeable battery 42 to charge the rechargeable battery 42. The power receiving coil 44 may be provided with electromagnetic signals by a dedicated wireless charging device. For example, the wireless charging device includes a power output coil. When the power receiving coil 44 is close (aligned) to the power output coil, the power output coil emits an electromagnetic signal to transfer power to the power receiving coil 44.

The monitor pad 40 in FIG. 5 does not require an external connection interface, does not need to provide additional openings for battery replacement, and does not need to provide a physical charging interface for rechargeable batteries. A user will not see any electrical interface on the monitor pad 40. In this way, the user experience can be improved. In addition, for example, in the case of using a connector or a battery, an interface/opening is usually provided for the connector/battery at a specific position (side) of the monitor pad 40, but the microphones Mic 1 and Mic 2 are located close to the center of the monitor pad 40. Therefore, a long wiring is required inside the monitor pad 40. In the embodiment of FIG. 5, since such an interface/opening is not required, the wiring length inside the monitor pad 40 can be reduced. This is beneficial to reduce the influence of electronic devices on the comfort/durability of the monitor pad 40.

Figure 6:
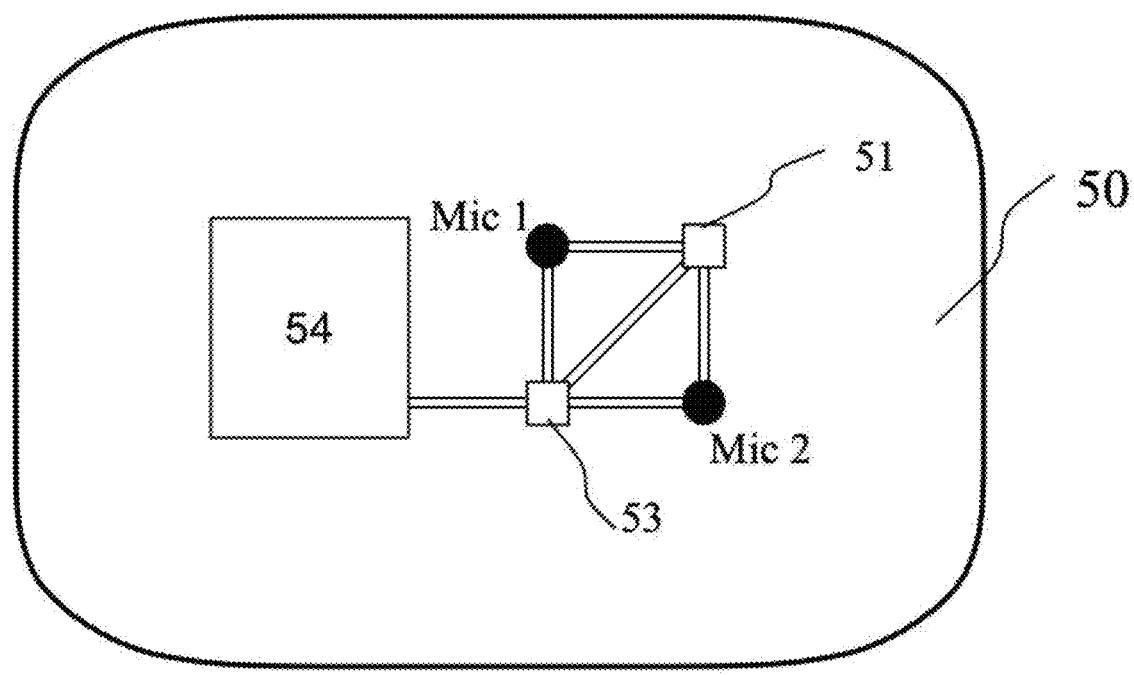
FIG. 6 shows a schematic structural diagram of a monitor pad according to another embodiment of this disclosure.

FIG. 6 shows a schematic structural diagram of a monitor pad according to another embodiment of this disclosure. In FIG. 6, the monitor pad 50 includes microphones Mic 1 and Mic 2. The transmission circuit includes a wireless transmission device 51. In addition, the monitor pad 50 further includes: a power receiving coil 54 and a rectifying circuit 53. The power receiving coil 54 receives an external electromagnetic signal, and the rectifier circuit 53 converts the external electromagnetic signal into direct current. The direct current is supplied to the microphones Mic 1 and Mic 2 and the wireless transmission device 51 to supply power to them. The microphones Mic 1 and Mic 2 and the wireless transmission device 51 can operate under the power provided by the power receiving coil 54. For example, an interrogation signal can be sent to the monitor pad 50 by an external interrogator. The power receiving coil 54 in the monitor pad 50 generates power for the microphones Mic 1 and Mic 2 and the wireless transmission device 51 in response to the interrogation signal.

Here, at least a part of the power receiving coil may serve as an antenna of the wireless transmission device. In this way, the quantity of electronic devices inside the monitor pad 50 can be saved.

In addition, this design can provide a simpler structure of the monitor pad 50, thereby helping to improve the portability of the monitor pad 50.

Figure 7:
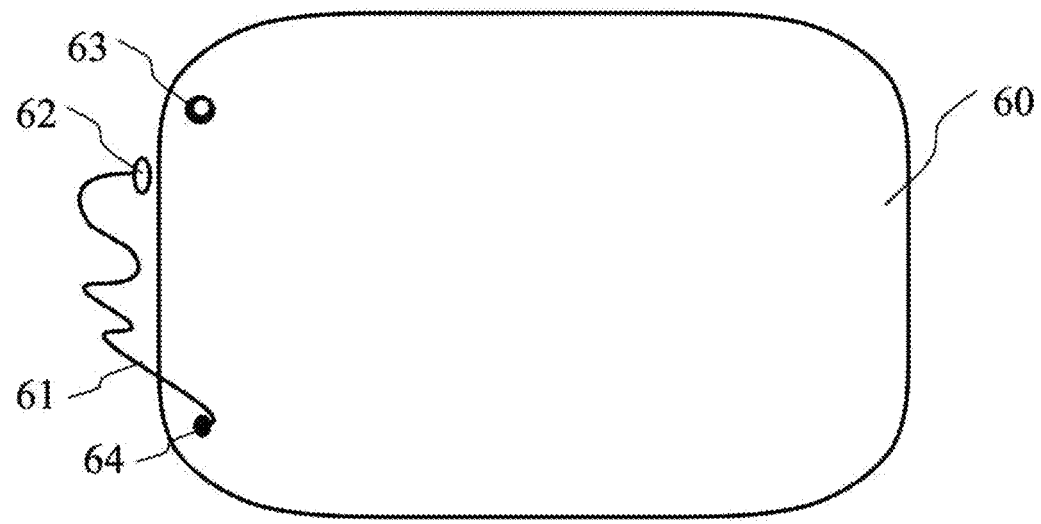
FIG. 7 shows a schematic structural diagram of a monitor pad according to another embodiment of this disclosure.
Figure 8:
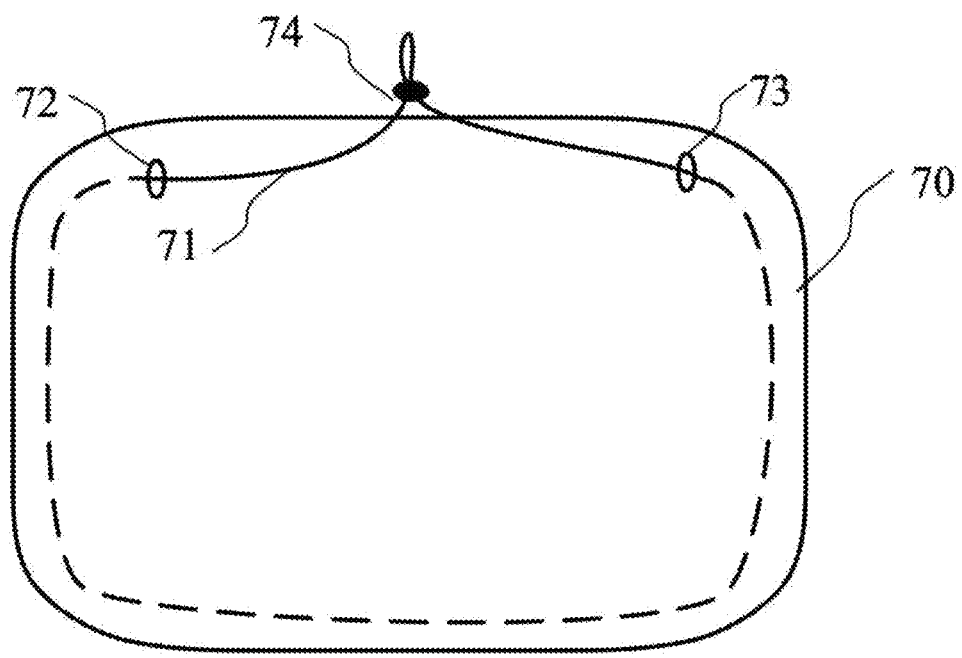
FIG. 8 shows a schematic structural diagram of a monitor pad according to another embodiment of this disclosure.

FIG. 7 shows a schematic structural diagram of a monitor pad according to another embodiment of this disclosure. FIG. 8 shows a schematic structural diagram of a monitor pad according to another embodiment of this disclosure. In the embodiment of FIGS. 7 and 8, the monitor pad includes a packing line and a packing locking structure. When the monitor pad is packed up, the packing line tightens the monitor pad towards the packing position, and the packing locking structure locks the packing line at the tightening position.

Specifically, in the embodiment of FIG. 7, one end 64 of the packing line 61 is fixed at a corner of a short edge of the monitor pad 60. A locking ring 62 is provided at the other end of the packing line 61. A locking button 63 is provided at the other corner of the aforementioned short edge of the monitor pad 60. When the monitor pad 60 is rolled up from the other short edge, the packing line 61 can be used to wind the rolled monitor pad 60, and after the packing line 61 is wound around the rolled monitor pad 60, the locking ring 62 and the locking button 63 can be used to secure the packing line 61 in the locked position of the winding.

In the embodiment of FIG. 8, the packing line 71 is arranged inside the monitor pad 70 along the three sides of the monitor pad 70 (shown by the dashed lines in FIG. 8). A part of the packing line 71 extends from the inside of the monitor pad 70 at the positions of the openings 72 and 73. A locking clip 74 is provided at the outer portion of the packing line 71. When the packing line 71 is pulled, the monitor pad 70 shrinks/folds. When the monitoring pad 70 reaches the desired locked state, the locking clip 74 is used to secure the packing line 71 in the locked position.

Here, the use of the packing structure can reduce the volume of the monitor pad during packing and/or secure the packing shape of the monitor pad, thereby facilitating the storage and carrying of the monitor pad.

Figure 9:
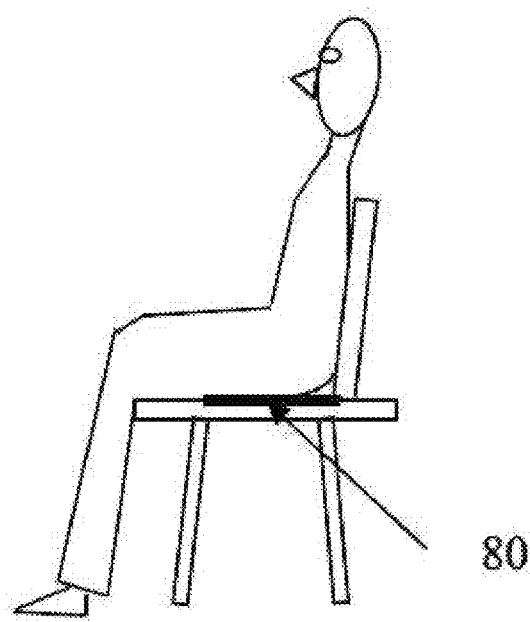
FIG. 9 shows a schematic diagram of an application scenario of a monitor pad according to another embodiment of this disclosure.

FIG. 9 shows a schematic diagram of an application scenario of a monitor pad according to another embodiment of this disclosure. In the application scenario of FIG. 9, the monitor pad 80 is placed on a chair and is used as a seat cushion. The monitor pad 80 monitors the user's physical body status while providing a soft and comfortable seat cushion.

Figure 10:
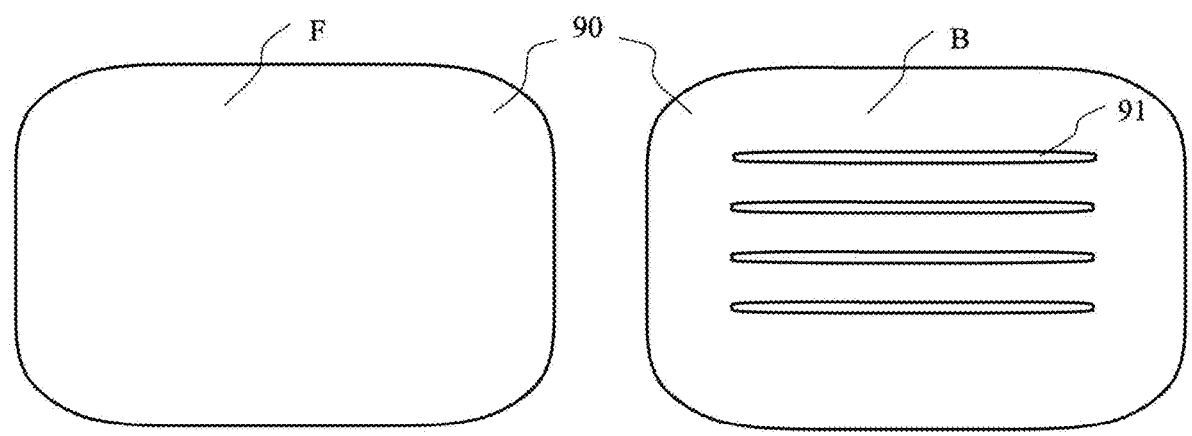
FIG. 10 shows a schematic structural diagram of a monitor pad according to another embodiment of this disclosure.

FIG. 10 shows a schematic structural diagram of a monitor pad according to another embodiment of this disclosure. In the case where the monitor pad serves as a seat cushion, when a user sits on a chair, the user may adjust the sitting posture randomly. When the user adjusts his sitting posture, the position of the monitor pad may change. For the microphone in the monitor pad, changes in the position of the monitor pad can generate noise, thereby affecting the monitoring results of the monitor pad. In order to avoid/mitigate the influence of such noise to a certain extent, a non-slip structure can be provided. As shown in FIG. 10, a non-slip structure is provided on one side (back side B) of the pad cover of the monitor pad 90. The anti-slip structure includes an anti-slip strip 91. The material of the anti-skid strip 91 may be silicone or rubber. The non-slip structure may not be provided on the other side (front side F) of the pad cover of the monitor pad 90.

Through this anti-skid structure, on the one hand, the sliding when a user sits on the monitor pad can be reduced, and the user experience can be improved; on the other hand, the influence of the sliding of the monitor pad on the monitoring result can be avoided.

Figure 11:
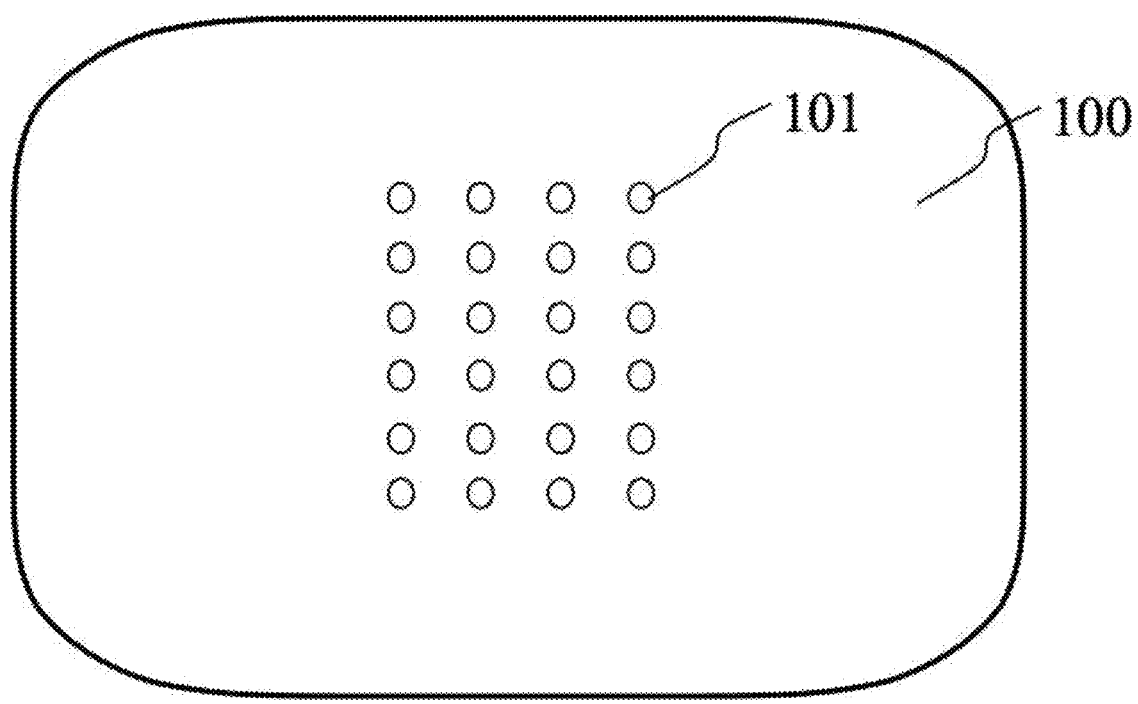
FIG. 11 shows a schematic structural diagram of a monitor pad according to another embodiment of this disclosure.

FIG. 11 shows a schematic structural diagram of a monitor pad according to another embodiment of this disclosure. The pad cover of the monitoring pad 100 shown in FIG. 11 includes a mesh structure 101. The mesh structure 101 is beneficial to improve the air permeability of the monitoring pad 100, thereby improving the comfort of the user during use.

Figure 12:
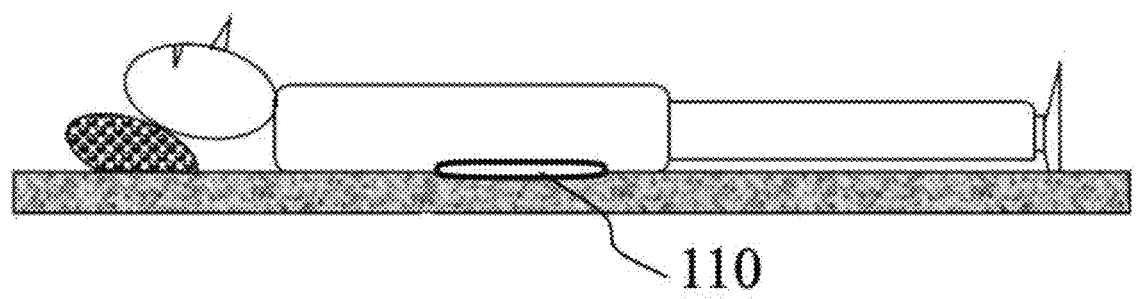
FIG. 12 shows a schematic diagram of an application scenario of a monitor pad according to another embodiment of this disclosure.

FIG. 12 shows a schematic diagram of an application scenario of a monitor pad according to another embodiment of this disclosure. In the application scenario of FIG. 12, the monitor pad 110 may be placed on a bed under a user's body. For example, the monitor pad can be placed on the bed, located under the back of the user. When the user uses the monitoring pad, the monitoring pad can support the user's waist, thereby reducing the pressure on the spine during sleep. This is helpful for alleviating lower back pain symptoms, such as sciatica, lumbar disc herniation, etc. In addition, the monitoring pad can also be placed on the bed, at the user's shoulder. This helps the user relax the muscles of the neck and shoulders during sleep, thereby improving the user's rest quality. The monitor pad 110 monitors the user's physical status while providing comfort to the user.

In another embodiment, the monitor pad 110 may also be located under a mattress or the like and correspond to the position of the user's heart.

Figure 13:
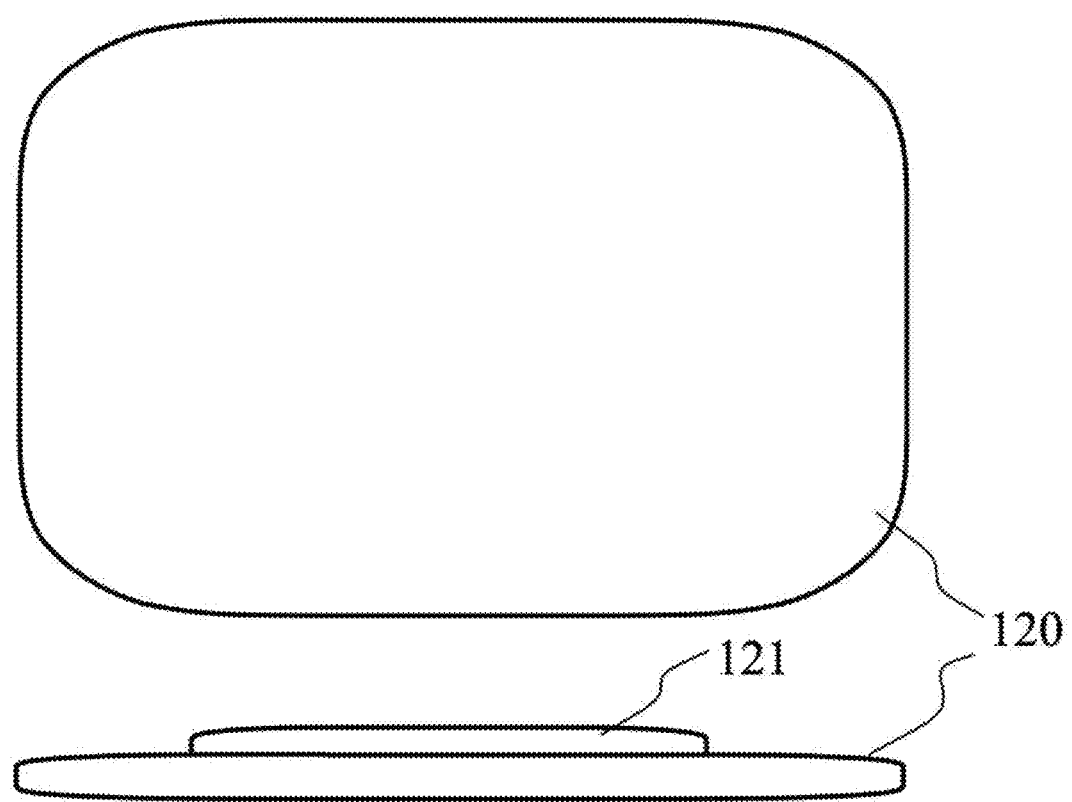
FIG. 13 shows a schematic structural diagram of a monitor pad according to another embodiment of this disclosure.

FIG. 13 shows a schematic structural diagram of a monitor pad according to another embodiment of this disclosure. As shown in FIG. 3, a convex portion 121 is provided in the middle area of the front surface of the monitor pad 120. When the monitor pad 120 is placed under the user's back, the convex portion 121 of the monitor pad 120 matches the curved contour of the user's back, thereby providing a better support effect. This also helps the user to maintain a fixed supine posture, thereby providing a stable monitoring signal output.

In addition, when the monitoring pad 120 is used on the user's shoulder position, its curved profile can also provide stronger support for the user's shoulder, thereby enhancing the user's experience.

Figure 14:
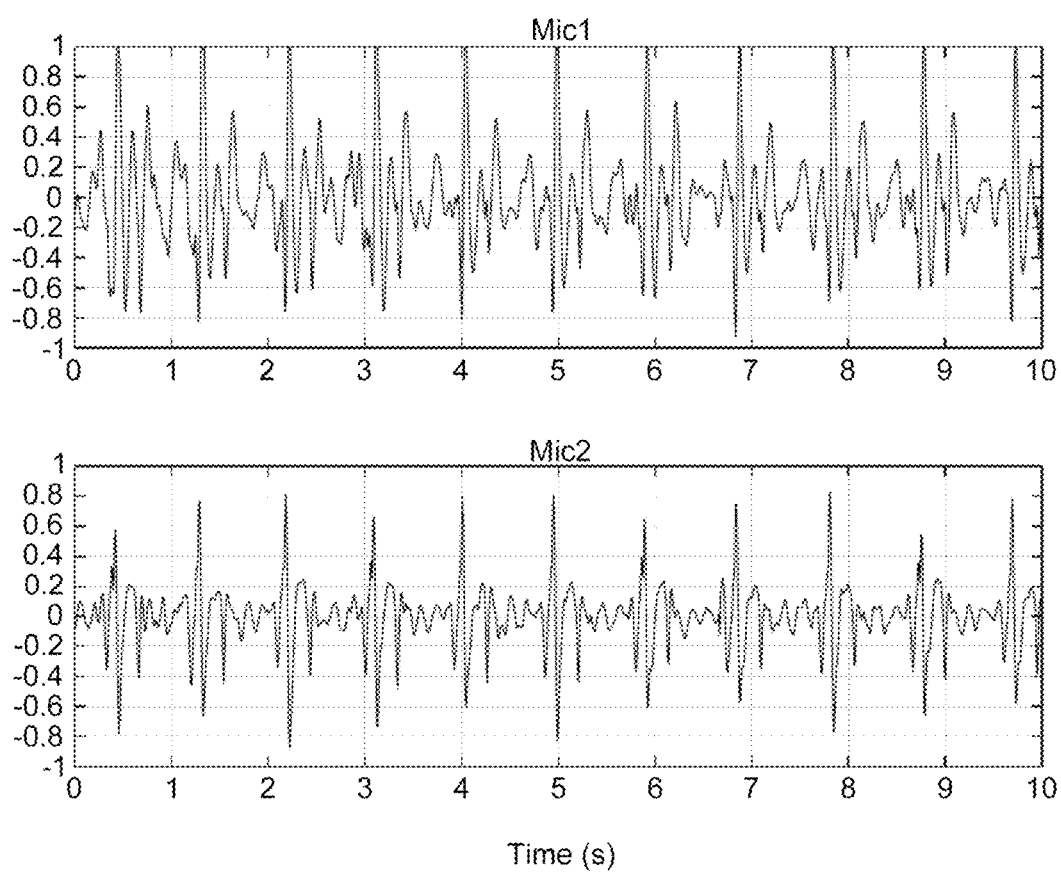
FIGS. 14-16 show schematic graphs of signals obtained by monitoring using a monitor pad according to another embodiment of this disclosure.
Figure 15:
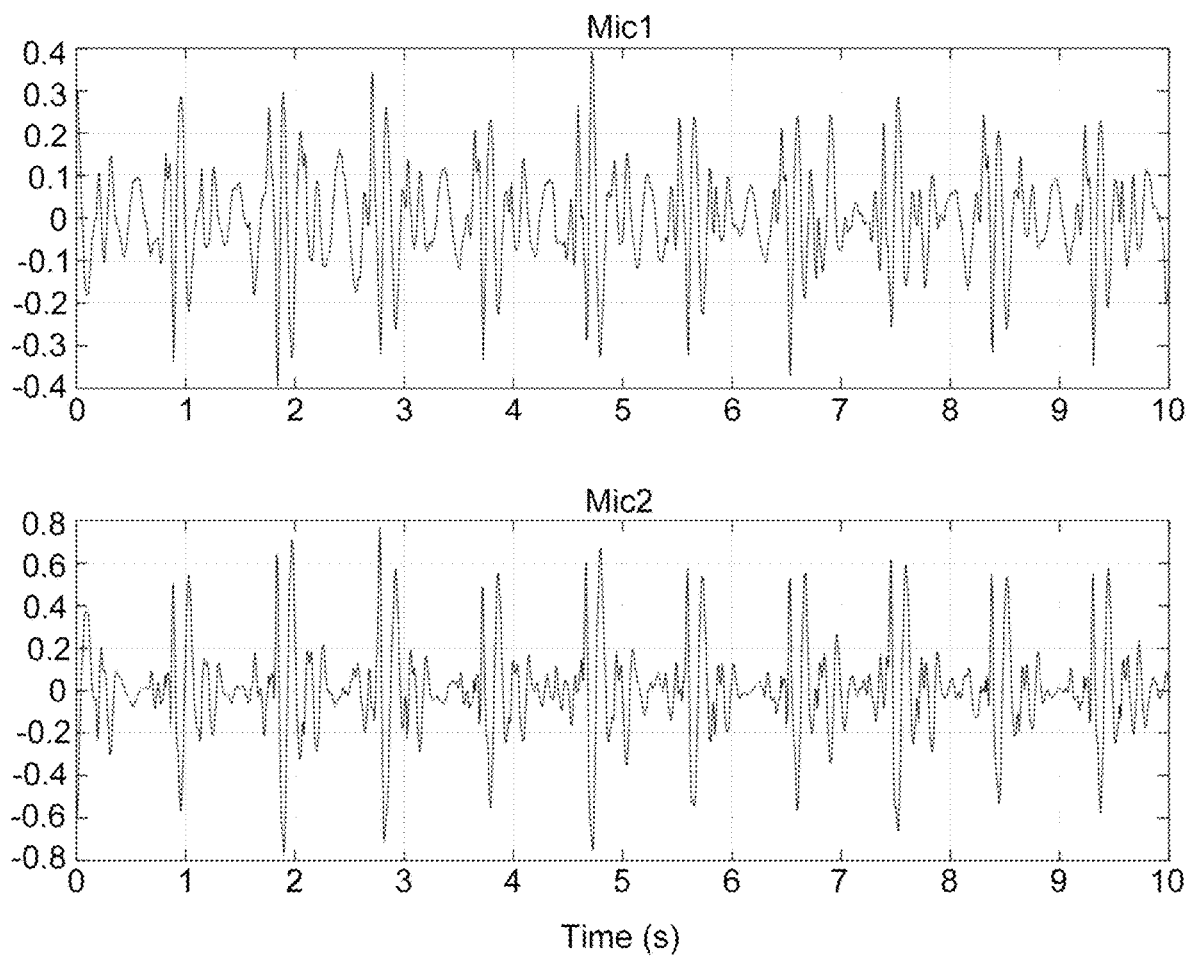
Figure 16:
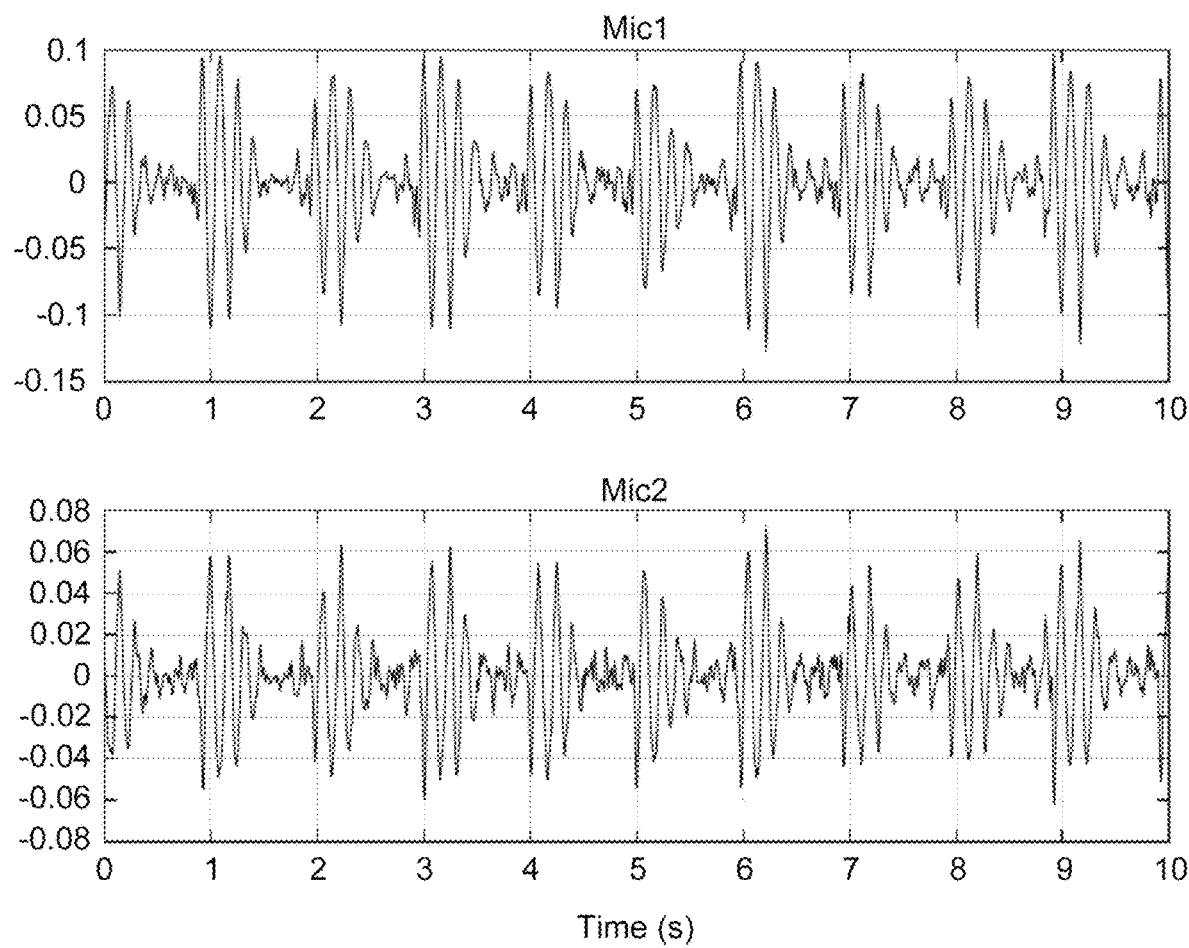

FIGS. 14-15 show schematic diagrams of signals obtained by monitoring using a monitor pad according to another embodiment of this disclosure. The horizontal axes in FIGS. 14-15 represent time, and the vertical axes represent the amplitude of the sampled signal. FIG. 14 shows the signals sampled by Mic 1 and Mic 2 of the monitor pad when a user is was face up lying on the bed. FIG. 15 shows the signals sampled by Mic 1 and Mic 2 of the monitor pad when a user is side lying on the bed. FIG. 16 shows the signals sampled by Mic 1 and Mic 2 of the monitor pad when the user is sitting on the bed. The user's heart rate can be calculated based on the signal.

It can be seen from FIGS. 14-16 that the usage of the monitor pad here can effectively detect the user's body information, thereby monitoring the user's physical status.

Figure 17:
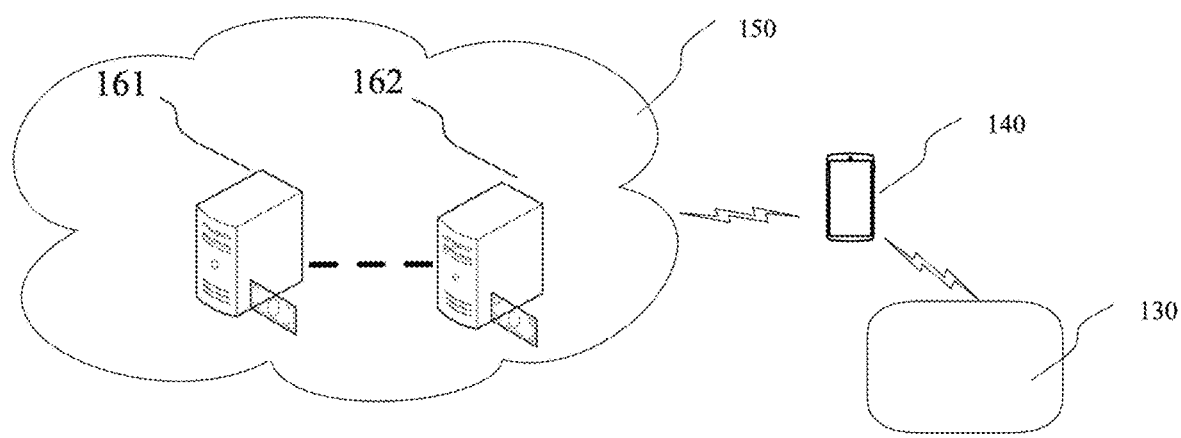
FIG. 17 shows a schematic structural diagram of a body monitoring system according to another embodiment of this disclosure.

FIG. 17 shows a schematic structural diagram of a body monitoring system according to another embodiment of this disclosure. As shown in FIG. 17, the body status monitoring system includes a monitor pad 130, an external processing device 140 and a network server 161 . . . 162. The monitor pad 130 is, for example, the monitor pad described above. The processing device 140 may be, for example, a smart phone, a tablet computer, a notebook computer, a processing device dedicated to monitor pads, and the like. The network server 161, . . . , 162 is located in the network 150.

The monitor pad 130 detects the user's body information and sends the detected body information to the external processing device 140. The external processing device 140 forwards the body information to the network servers 161, . . . , 162 to analyze the body information. The network server 161, . . . , 162 may return the analysis result to the processing device 140 for the reference of the user and/or an expert.

Although some specific embodiments of the disclosure have been demonstrated in detail with examples, it should be understood by a person skilled in the art that the above examples are only intended to be illustrative but not to limit the scope of the disclosure.

What is claimed is:

1. A monitor pad, including: a pad cover, a padding, a microphone and a transmission circuit,
    wherein the microphone is positioned in the padding and is adapted to detect body information of a person proximate to the monitor pad, and the transmission circuit is adapted to transmit the body information to an external processing device for processing the body information,
    further comprising: a power receiving coil and a rectifier circuit,
    wherein the transmission circuit includes a wireless transmission device,
    wherein, the power receiving coil is adapted to receive an external electromagnetic signal, the rectifier circuit is adapted to convert the external electromagnetic signal into a direct current for provision to the microphone and the wireless transmission device, and
    wherein at least a part of the power receiving coil serves as an antenna of the wireless transmission device,
    the microphone comprises two microphones, which are symmetrical with respect to a center of the monitor pad and have an angle of 45 degrees with a short axis or a long axis of the monitor pad, respectively.

2. The monitor pad according to claim 1, wherein the monitor pad is foldable, and having a length less than or equal to 420 mm and a width less than or equal to 297 mm.

3. The monitor pad according to claim 1, wherein the body information is selected from the group consisting of a person's heartbeat signal and a breathing vibration signal.

4. The monitor pad according to claim 1, wherein a non-slip structure is provided on one side of the pad cover, the non-slip structure includes at least one non-slip strip, and the non-slip strip comprises silicone or rubber.

5. The monitor pad according to claim 1, further comprising: a packing line and a packing locking structure, so that when the monitor pad is packed up, the packing line is adapted to tighten the monitor pad towards a packing position, and the packing locking structure is adapted to lock the packing line at a tightening position.

6. The monitor pad according to claim 1, wherein the transmission circuit includes a connector, wherein the microphone is connected to the connector, and the connector is adapted to connect with the processing device to send the body information to the processing device.

7. The monitor pad according to claim 1, further comprising: a battery, wherein, the microphone and the wireless transmission device are connected to the battery to receive power, and the microphone is connected to the wireless transmission device to transmit the body information to the processing device via the wireless transmission device.

8. The monitor pad according to claim 7, wherein the battery is a rechargeable battery, the direct current is supplied to the rechargeable battery to charge the battery.

9. A body status monitoring system, including:
    the monitor pad according to claim 1;
    an external processing device; and
    a network server,
    wherein the monitor pad is adapted to detect body information of a person and send the detected body information to an external processing device, and the external processing device is adapted to forward the body information to the network server to analyze the body information.

10. The monitor pad according to claim 1, further comprising a convex portion provided in a middle area of a front surface of the monitor pad and adapted to match a curved contour of an user.

* * * * *